(12) United States Patent
Sgroi, Jr. et al.

(10) Patent No.: US 10,117,656 B2
(45) Date of Patent: Nov. 6, 2018

(54) LOADING UNIT LOCKING COLLAR

(71) Applicant: Covidien LP, Mansfield, MA (US)

(72) Inventors: Anthony Sgroi, Jr., Wallingford, CT (US); Christopher Penna, Guilford, CT (US)

(73) Assignee: Covidien LP, Mansfield, MA (US)

( * ) Notice: Subject to any disclaimer, the term of this patent is extended or adjusted under 35 U.S.C. 154(b) by 547 days.

(21) Appl. No.: 14/810,811

(22) Filed: Jul. 28, 2015

(65) Prior Publication Data
US 2016/0192939 A1 Jul. 7, 2016

Related U.S. Application Data

(63) Continuation-in-part of application No. 14/591,193, filed on Jan. 7, 2015.

(51) Int. Cl.
*A61B 17/115* (2006.01)
*A61B 17/00* (2006.01)
(Continued)

(52) U.S. Cl.
CPC . *A61B 17/1155* (2013.01); *A61B 2017/00473* (2013.01); *A61B 2017/07271* (2013.01); *A61B 2017/2946* (2013.01)

(58) Field of Classification Search
CPC .. A61B 2017/2946; A61B 2017/07271; A61B 2017/00473; A61B 17/1155
(Continued)

(56) References Cited

U.S. PATENT DOCUMENTS 3,193,165 A 7/1965 Akhalaya et al.
3,388,847 A 6/1968 Kasulin et al.
(Continued)

FOREIGN PATENT DOCUMENTS

CA 908529 A 8/1972
CN 201481477 U 5/2010
(Continued)

OTHER PUBLICATIONS

European Search Report dated May 10, 2016, issued in EP Application No. 15198203.
(Continued)

*Primary Examiner* — Robert Long
*Assistant Examiner* — Xavier A Madison

(57) ABSTRACT

A loading unit assembly includes a shell assembly and a locking collar. The shell assembly has a proximally extending annular ring that defines a cylindrical opening. The annular ring defines a lock opening that passes through the annular ring. The shell assembly defines a retention slot that is adjacent the annular ring on an opposite side of the annular ring from the lock opening. The locking collar is positioned about the annular ring and has a body, a lock, and a retention tab. The body includes a release surface. The locking collar has a locked configuration wherein the lock extends into the cylindrical opening and an unlocked configuration wherein the lock is disposed outwardly of the cylindrical opening. The side of the locking collar opposite the lock is prevented from moving outwardly in relation to the annular ring when the release surface is pressed inwardly towards the annular ring.

20 Claims, 13 Drawing Sheets

(51) Int. Cl.
*A61B 17/072* (2006.01)
*A61B 17/29* (2006.01)

(58) Field of Classification Search
USPC .......... 227/175.1–182.1; 606/300, 138, 215
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |

(56) References Cited

U.S. PATENT DOCUMENTS

| | | |
|---|---|---|
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |

(56) References Cited

U.S. PATENT DOCUMENTS

| | | |
|---|---|---|
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,789,737 B2 | 7/2014 | Hodgkinson et al. |
| 2003/0111507 A1 | 6/2003 | Nunez |
| 2004/0059227 A1 | 3/2004 | Nita et al. |
| 2004/0194324 A1 | 10/2004 | Youn-Chyuan |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0179375 A1 | 7/2008 | Scirica |
| 2008/0308605 A1 | 12/2008 | Scirica |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0326540 A1 | 12/2009 | Estes |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0186614 A1 | 8/2011 | Kasvikis |
| 2011/0192882 A1 | 8/2011 | Hess et al. |
| 2011/0276036 A1 | 11/2011 | Spranger et al. |
| 2012/0054979 A1* | 3/2012 | Dant .......... A47L 9/0072 15/347 |
| 2012/0061448 A1 | 3/2012 | Lingman |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |

(56) References Cited

U.S. PATENT DOCUMENTS

| | | |
|---|---|---|
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0096591 A1 | 4/2013 | Hart et al. |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0123705 A1 | 5/2013 | Holm et al. |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181029 A1 | 7/2013 | Milliman |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0309677 A1 | 10/2014 | Baldwin |
| 2015/0108201 A1 | 4/2015 | Williams |
| 2015/0320420 A1 | 11/2015 | Penna et al. |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3042619 A1 | 7/2016 |
| FR | 1136020 A | 5/1957 |
| FR | 1461464 A | 2/1966 |
| FR | 1588250 A | 4/1970 |
| FR | 2243758 A1 | 4/1975 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9805261 A2 | 2/1998 |
| WO | 2001/054594 A1 | 8/2001 |
| WO | 2004107990 A1 | 12/2004 |
| WO | 2008/107918 A1 | 9/2008 |
| WO | 2012015917 A1 | 2/2012 |
| WO | 2014139327 A1 | 9/2014 |
| WO | 2014139440 A1 | 9/2014 |
| WO | 2014139442 A1 | 9/2014 |
| WO | 2014139467 A1 | 9/2014 |
| WO | 20140139442 A1 | 9/2014 |

OTHER PUBLICATIONS

European Search Report dated May 17, 2016, issued in EP Application No. 16150284.

European Search Report dated Jun. 24, 2016, issued in EP Application No. 16150288.5.

European Search Report dated Sep. 1, 2016, issued in EP 16166326.

European Search Report dated Nov. 30, 2016, issued in EP Application No. 16181395.

U.S. Appl. No. 14/591,193, filed Jan. 7, 2015, inventor: Sgroi, Jr.

U.S. Appl. No. 14/805,547, filed Jul. 22, 2015, inventor: Scirica, et al.

U.S. Appl. No. 14/859,590, filed Sep. 21, 2015, inventor: Sgroi.

U.S. Appl. No. 62/100,512, filed Jan. 7, 2015, inventor: Williams et al.

U.S. Appl. No. 62/150,913, filed Apr. 22, 2015, inventor: Penna et al.

U.S. Appl. No. 14/804,814, filed Jul. 21, 2015, inventor: Williams.

EP Examination Report dated Jun. 20, 2017, issued in EP Application No. 16150288.

European Search Report dated May 23, 2017, issued in EP Application No. 16189648.

Partial European Search Report dated Jan. 16, 2017, issued in EP Appln. No. 16180339.

* cited by examiner

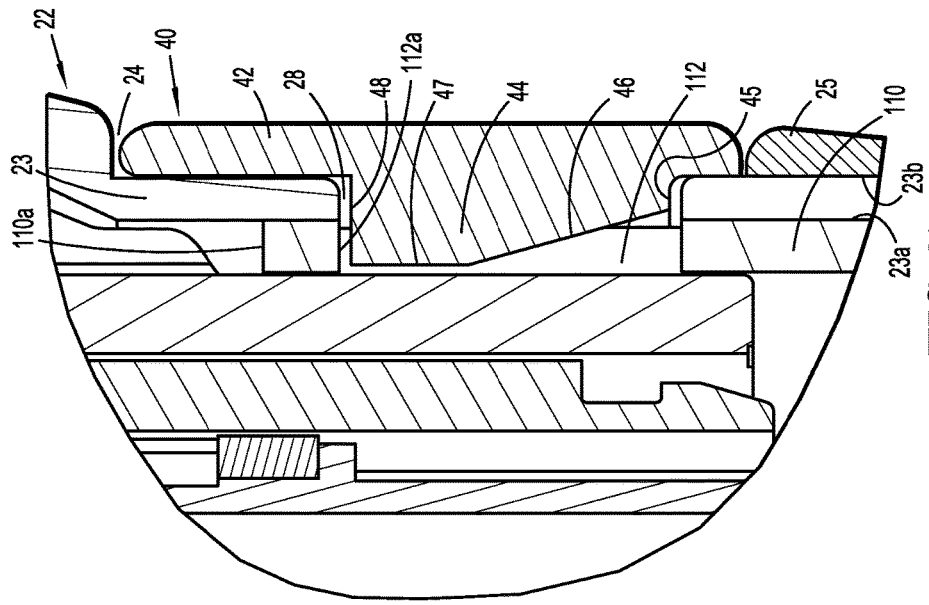

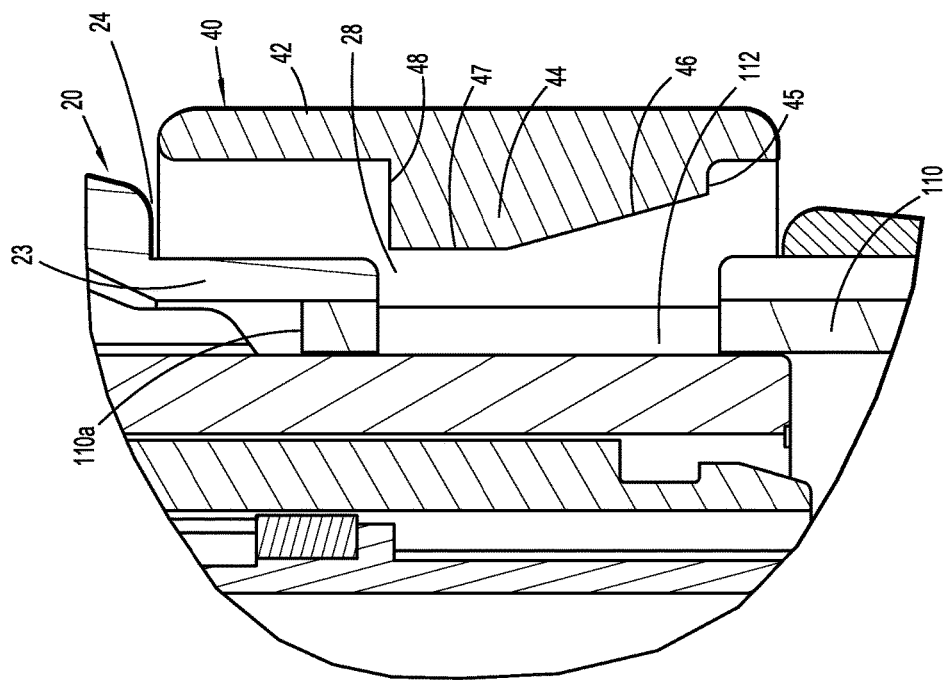
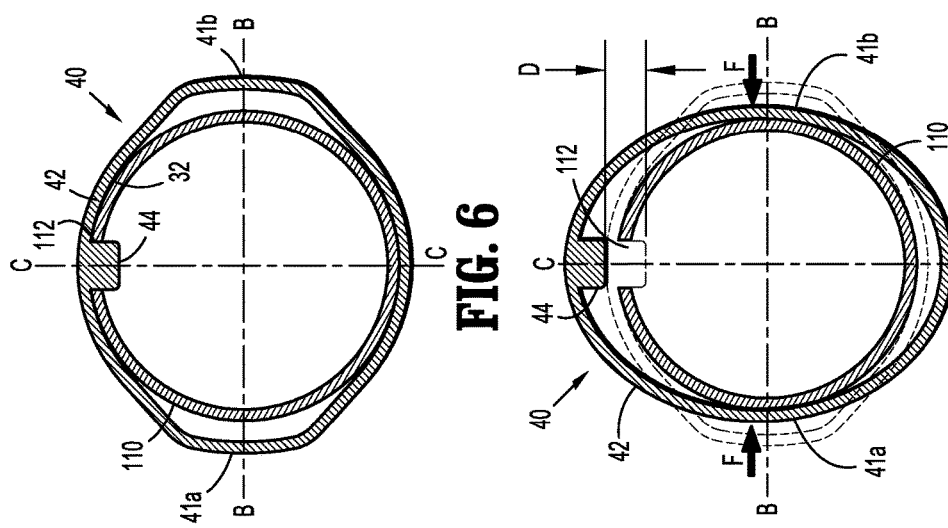

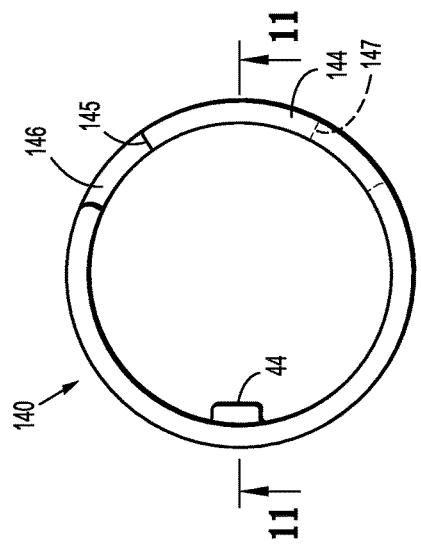
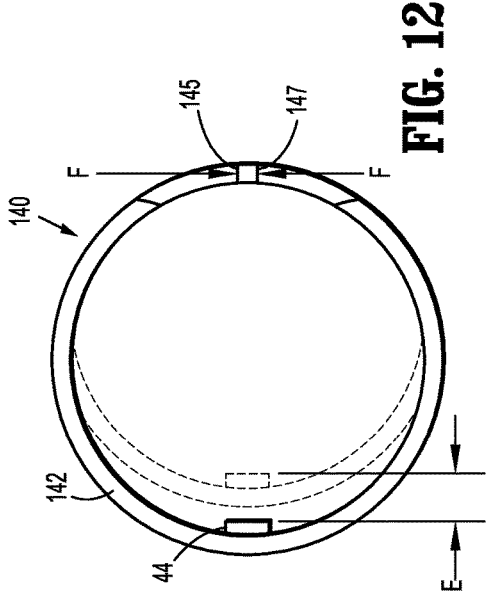
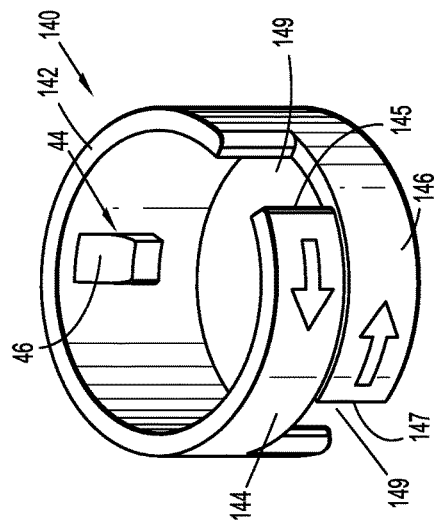
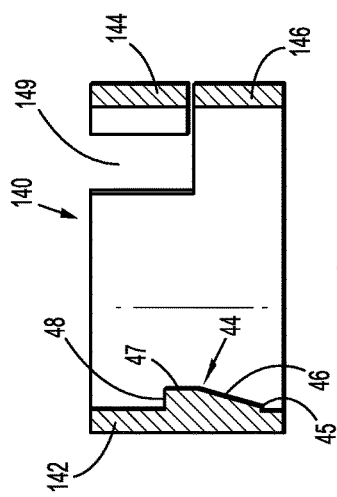
FIG. 10
FIG. 12
FIG. 9
FIG. 11

LOADING UNIT LOCKING COLLAR

CROSS-REFERENCE TO RELATED APPLICATION

This application is a continuation-in-part and claims the benefit of, and priority to, U.S. patent application Ser. No. 14/591,193, filed Jan. 7, 2015, the entire contents of which are hereby incorporated herein by reference.

BACKGROUND

1. Technical Field

The present disclosure relates generally to surgical stapling instruments. More specifically, the present disclosure relates to circular surgical stapling instruments including replaceable loading units.

2. Background of Related Art

Surgical stapling devices configured to join tissue portions during a surgical procedure are well known. These devices include linear end effectors which are oriented parallel or transverse to a longitudinal axis of the device as well as circular end effectors. Typically, linear stapling devices include a disposable loading unit or a replaceable cartridge that allows the stapling device to be used multiple times. However, conventional circular stapling devices include a cartridge or shell assembly that is fixedly attached to the device such that the device must be disposed of after a single use. Some circular stapling devices include a cartridge or shell assembly that is replaceable.

A need exists in the art for a simple, inexpensive device for releasably securing a cartridge or shell assembly to a circular stapling device to facilitate reuse of the stapling device.

SUMMARY

In an aspect of the present disclosure, a loading unit and locking collar assembly includes a shell assembly and a locking collar. The shell assembly has a proximal end portion for receiving a distal end portion of a surgical instrument. The proximal end portion includes an annular ring that has an outer surface and an inner surface. The outer surface of the annular ring defines an annular groove with the proximal end portion. The annual ring defines a lock opening therethrough. The locking collar is releasably disposed within the annular groove and includes an annular body. The annular body of the locking collar has a pair of release surfaces and a lock. The lock extends radially inward from the annular body. The pair of release surfaces is configured to transition the locking collar from a locked configuration to an unlocked configuration. In the locked configuration, the lock extends through the lock opening to penetrate the inner surface of the annular ring and in the unlocked configuration the lock is positioned radially outward from the inner surface of the annular ring.

In aspects, each of the release surfaces is urged towards the other release surface to transition the locking collar from the locked configuration to the unlocked configuration. Each of the release surfaces may be compressed radially inward to transition the locking collar towards the unlocked configuration. Alternatively, each of the release surfaces may be urged about the circumference of the locking collar in a plane transverse to a longitudinal axis of the shell assembly to transition the locking collar towards the unlocked configuration.

In some aspects, the locking collar defines an elliptical cross-section in a plane transverse to a longitudinal axis of the shell assembly in which the width in the unlocked configuration is less than the width in the locked configuration. The width may be defined between the pair of release surfaces. Alternatively, the locking collar may define an elliptical cross-section in a plane transverse to a longitudinal axis of the shell assembly in which the width is less than the height.

In certain aspects, the locking collar defines a circular cross-section in a plane transverse to a longitudinal axis of the shell assembly in the locked configuration. The locking collar may define an elliptical cross-section in a plane transverse to a longitudinal axis of the shell assembly in which the width is less than the height in the unlocked configuration. The height may be defined between the pair of release surfaces and the lock.

In particular aspects, the locking collar is biased towards the locked configuration. The annular body of the locking collar may split to from the first and second release surfaces. The first release surface may extend in a first direction about the circumference of the annular body and the second release surface may extend in a second direction opposite the first direction about the circumference of the annular body. The first and second release surfaces may each include an end that defines an engagement window between the end and the annular body. The locking collar may be configured to provide indicia when the locking collar transitions from the unlocked configuration to the locked configuration. The indicia may be audible. The shell assembly may be configured to fire staples through tissue.

In another aspect of the present disclosure, a surgical system includes a surgical instrument, a loading unit, and a locking collar. The surgical instrument includes a distal end. A loading unit includes a shell assembly that has a proximal end portion positioned over the distal end of the surgical instrument. The proximal end portion includes an annular ring that has an outer surface and an inner surface. The outer surface of the annular ring defines an annular groove with the proximal end portion. The annular ring defines a lock opening therethrough. The locking collar is releasably disposed within the annular groove of the loading unit and includes an annular body that has a pair of release surfaces and a lock. The lock extends radially inward from the annular body. The pair of release surfaces is configured to transition the locking collar from a locked configuration to an unlocked configuration. In the locked configuration the lock extends through the lock opening to penetrate the inner surface of the annular ring and in the unlocked configuration the lock is positioned radially outward from the inner surface of the annular ring.

In aspects, the distal end of the surgical instrument defines a window. The lock may extend into the window in the locked configuration and may be positioned outside the window in the unlocked configuration. The locking collar may secure the loading unit to the distal end of the surgical instrument in the locked configuration and the locking collar may allow the loading unit to be removed from the surgical instrument in the unlocked configuration. The lock may include a proximal step, a distal step, and an angled surface between the proximal and distal steps. The angled surface may be configured to slide over the distal end portion of the surgical instrument to move the lock radially outward until the lock is positioned within windows defined in the distal end of the surgical instrument.

In another aspect of the present disclosure, a loading unit and locking collar assembly includes a shell assembly and a locking collar. The shell assembly has a proximally extending annular ring that defines a cylindrical opening. The annular ring defines a lock opening that passes through the annular ring. The shell assembly defines a first retention slot that is adjacent the annular ring on an opposite side of the annular ring from the lock opening. The locking collar is positioned about the annular ring. The locking collar has a body, a lock, and a first retention tab. The body includes at least one release surface. The lock extends from an inner surface of the body spaced from the at least one release surface. The locking collar has a locked configuration and an unlocked configuration. In the locked configuration, the lock extends through the lock opening into the cylindrical opening. In the unlocked configuration, the lock is disposed outwardly of the cylindrical opening. The first retention tab is received within the first retention slot to prevent a side of the locking collar opposite the lock from moving outwardly in relation to the annular ring when the at least one release surface is pressed inwardly towards the annular ring.

In aspects, the at least one release surface includes two release surfaces positioned on opposite sides of the body. The two release surfaces may be moveable inwardly towards one another to transition the locking collar to the unlocked configuration. The annular ring may define a relief groove adjacent each of the two release surfaces. The release grooves may allow inward movement of the body of the locking collar in the area of the release surfaces. The body may be resilient and the resilience of the body may urge the locking collar towards the locked configuration.

In some aspects, the assembly includes a retention ring that is positioned about the annular ring proximal of the locking collar. The retention ring may define a second retention slot. The locking collar may include a second retention tab that is received within the second retention slot to prevent the side of the locking collar opposite the lock from moving outwardly when the at least one release surface is pressed inwardly towards the annular ring. The first and second retention tabs may be axially aligned with one another.

In particular aspects, the annular ring defines a retention groove that extends in a direction parallel to a longitudinal axis of the shell assembly. The first and second retention tabs extend from opposite sides of a retention rib that extends inwardly from an inner surface of the body. The retention rib may be disposed in the retention groove. The shell assembly may include a cover that extends distally over the retention groove to define the first retention slot. The body of the locking collar may define a cutout positioned adjacent the first retention tab. The cutout may be sized to receive the cover of the shell assembly.

In certain aspects, the annular ring defines retention openings that pass through the annular ring. The retention ring may include locking tabs that extend from an inner surface of the retention ring which are each received in a respective one of the retention openings to fix the retention ring to the annular ring. The retention openings may be unequally spaced about the annular ring. The locking tabs may define a wedge shape with an angled surface of the wedge facing distally. A proximal end of the annular ring may define chamfers that are each axially aligned with each of the retention openings and/or the lock opening.

In another aspect of the present disclosure, a surgical system includes a surgical instrument, a shell assembly, and a locking collar. The surgical instrument includes a distal end that defines a lock window through the distal end. The shell assembly has a proximally extending annular ring that defines a cylindrical opening. The annular ring defines a lock opening that passes through the annular ring. The shell assembly defines a first retention slot adjacent the annular ring on an opposite side of the annular ring from the lock opening. The distal end of the surgical instrument is received within the cylindrical opening with the lock opening radially aligned with the lock window. The locking collar is positioned about the annular ring. The locking collar has a body, a lock, and a first retention tab. The body includes a release surface. The lock extends from an inner surface of the body spaced apart from the release surface. The locking collar has a locked configuration and an unlocked configuration. In the locked configuration, the lock extends into the lock windows to secure the shell assembly to the distal end of the surgical instrument. In the unlocked configuration, the lock is disengaged from the lock window such that the shell assembly is detachable from the distal end of the surgical instrument. The first retention tab is received within the first retention slot to prevent a side of the locking collar opposite the lock from moving outwardly in relation to the annular ring when the release surface is pressed inwardly towards the annular ring.

In another aspect of the present disclosure, a method of using a loading unit includes aligning a locking collar with a shell assembly and sliding the loading unit distally over a proximally extending annular ring of the shell assembly. A lock of the locking collar engages the annular ring such that the lock is moved outwardly towards an unlocked configuration of the locking collar until the lock is aligned with a lock opening defined through the annular ring. Resilience of a body of the lock collar urges the locking collar towards a locked configuration of the locking collar to move the lock through the lock opening. A retention tab of the locking collar is positioned on an opposite side of the locking collar from the lock and slides into a retention slot defined by the shell assembly to prevent the opposite side of the locking collar from moving outwardly.

In aspects, the method includes attaching the loading unit to a distal end of a surgical instrument by aligning the loading unit with the distal end of the surgical instrument and sliding the loading unit over the distal end of the surgical instrument such that the lock of the locking engages the distal end of the surgical instrument. The distal end may move the lock outwardly to urge the locking collar towards the unlocked configuration until the lock is aligned with a locking window defined in the distal end of the surgical instrument. The lock may be urged through the locking window by resilience of the body of the locking collar to secure the loading unit to the distal end of the surgical instrument.

In some aspects, the method includes actuating a shell assembly of the loading unit with the surgical instrument after the loading unit is attached to the distal end of the surgical instrument. The method may include detaching the loading unit from the distal end of the surgical instrument after actuating the shell assembly by moving a release surface of the locking collar inwardly to move the lock outwardly and sliding the loading unit off of the distal end of the surgical instrument. Moving the release surface of the locking collar inwardly may disengage the lock from the locking window of the distal end of the surgical instrument. The retention tab of the locking collar may engage the shell assembly to prevent the side of the locking collar opposite the lock from moving outwardly in response to moving the release surface of the locking collar inwardly.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 3 is an enlarged side view of the distal end of the surgical instrument and loading unit of FIG. 1A;

FIG. 4 is a side cross-sectional view taken along the longitudinal axis of FIG. 3;

FIG. 5 is an enlarged view of the indicated area of detail of FIG. 4;

FIG. 6 is a partial cross-sectional view taken along the section line 6-6 of FIG. 4 illustrating showing the distal end of the surgical instrument and the locking collar in the locked configuration;

FIG. 7 is a partial cross-sectional view similar to FIG. 6 with the distal end of the adapter and the locking collar in the unlocked configuration with a locked configuration of the locking collar shown in dashed lines;

FIG. 8 is an enlarged side cross-sectional view similar to FIG. 5 with the locking collar in the unlocked configuration;

FIG. 9 is a perspective view of another locking collar in accordance with the present disclosure;

FIG. 10 is a front view of the locking collar of FIG. 9 in a locked configuration;

FIG. 11 is a cross-sectional view taken along the section line 11-11 of FIG. 10;

FIG. 12 is an end view of the locking collar of FIG. 9 in an unlocked configuration with a locked configuration of the locking collar shown in dashed lines;

DETAILED DESCRIPTION OF EMBODIMENTS

Figure 1A:
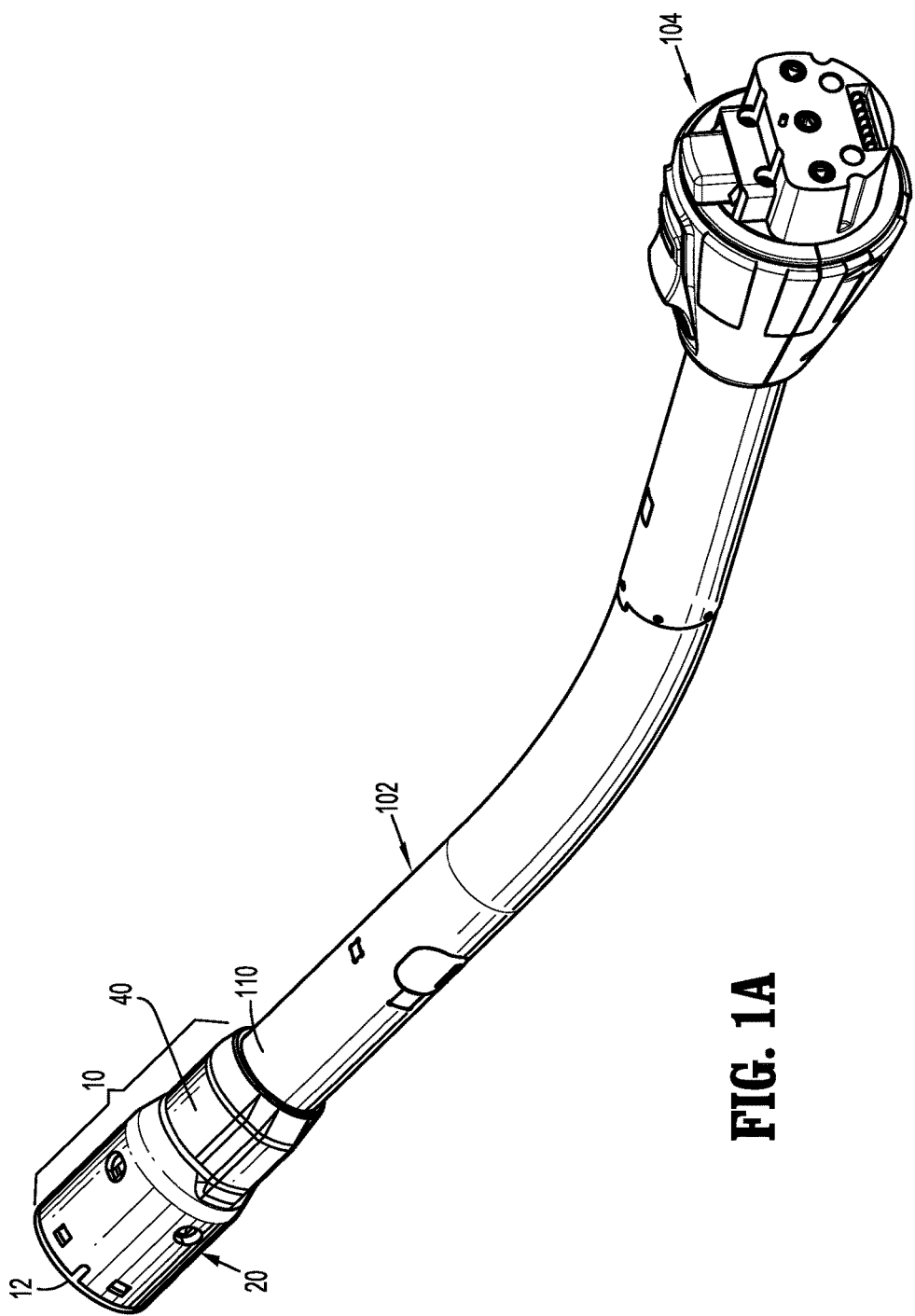
FIG. 1A is a perspective view of a circular stapling surgical instrument in accordance with the present disclosure with a loading unit releasably coupled to a distal end of the surgical instrument.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 1B:
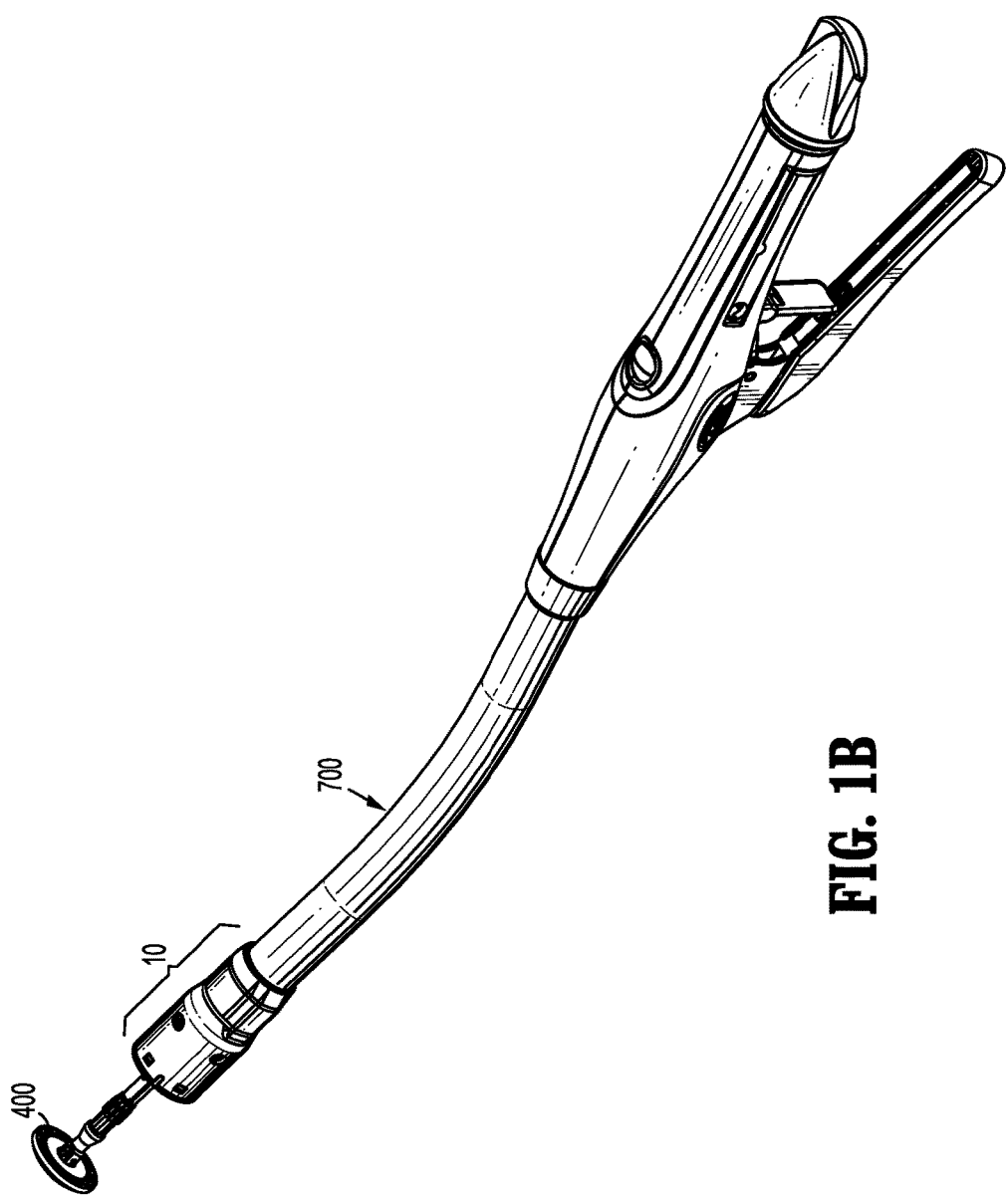
FIG. 1B is a perspective view of another circular stapling adapter in accordance with the present disclosure with the loading unit of FIG. 1A releasably coupled to a distal end of the surgical instrument.
Figure 2A:
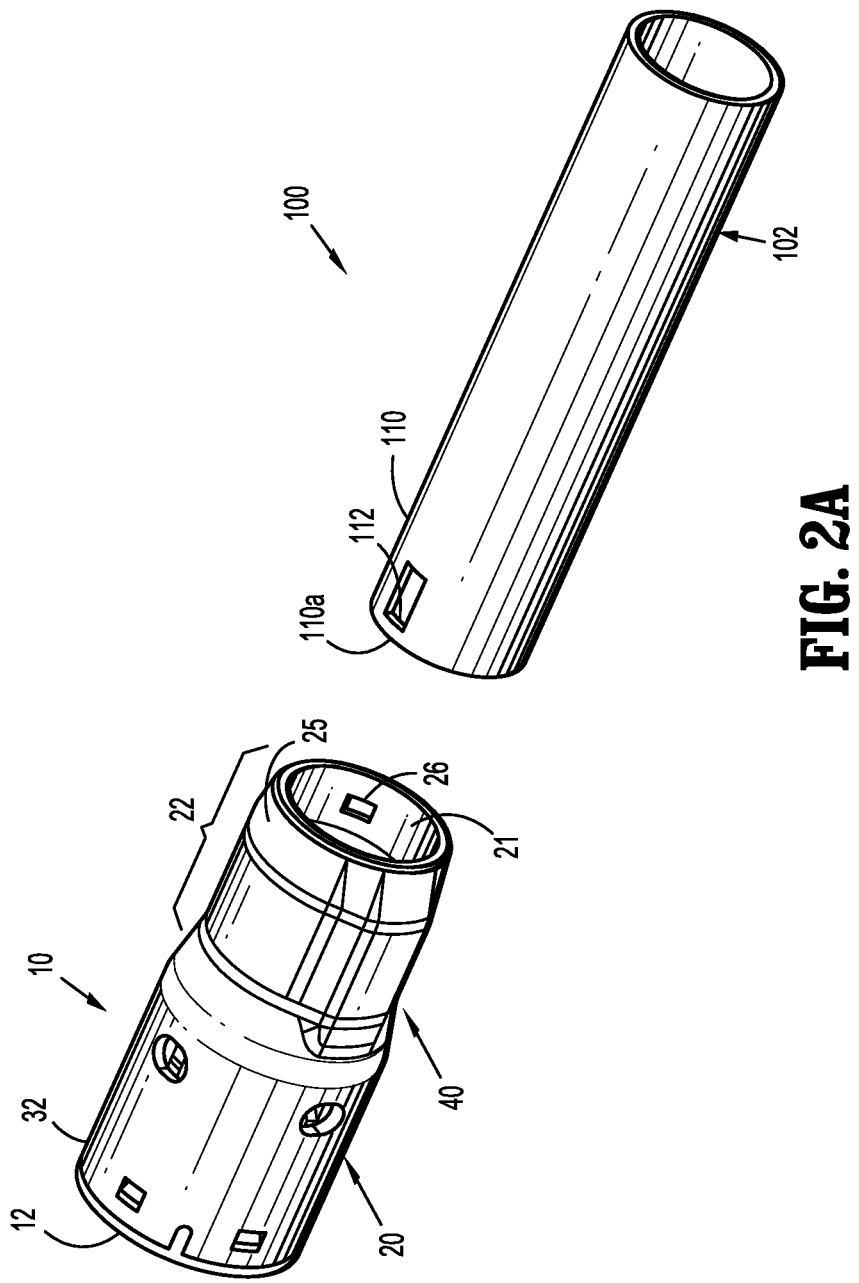
FIG. 2A is a perspective view of the adapter of FIG. 1A with the loading unit decoupled from the surgical instrument.

With reference to FIGS. 1A and 2A, a loading unit 10 is provided in accordance with an embodiment of the present disclosure. The loading unit 10 is configured for selective connection to a powered hand held electromechanical instrument (not shown) via an adapter 102 of a surgical instrument. Alternatively, the loading unit 10 can be configured for connection directly to a manually actuated handle assembly or stapling instrument 700 (FIG. 1B) such as described in U.S. Pat. No. 8,789,737 ("the '737 Patent"), which is incorporated in its entirety herein by reference. In the embodiment illustrated in FIGS. 1A and 2A, the loading unit 10 is releasably coupled to a distal end portion 110 of the adapter 102 and includes a staple cartridge 12 (FIG. 4), a shell assembly 20, and a locking collar 40. The loading unit 10 may also include an anvil 400 as shown in the illustrative embodiment of FIG. 1B. The adapter 102 is configured to translate movement of a stapling instrument, e.g., an electromechanical instrument (not shown), to actuate the staple cartridge 12 to suture and cut tissue (not shown). A proximal end 104 of the adapter 102 is attachable to the stapling instrument to actuate the staple cartridge 12. It is contemplated that the proximal end 104 of the adapter 102 may be attached to a manually actuated instrument such as described in the '737 Patent to actuate the staple cartridge 12.

For a detailed description of the structure and function of an exemplary adapter and loading unit, please refer to commonly owned U.S. Provisional Patent Application Ser. No. 62/066,518, filed Oct. 21, 2014, and entitled "Adapter, Extension, and Connector Assemblies for Surgical Devices." For a detailed description of the structure and function of an exemplary electromechanical instrument, please refer to U.S. Patent Publication No. 2012/0253329. Each of these applications is incorporated herein by reference in its entirety.

Referring to FIG. 2A, the distal end portion 110 of surgical instrument, e.g., the adapter 102, defines a window 112. The window 112 passes through the outer surface of the distal end portion 110 of the adapter 102 and is spaced-apart from a distal end 110a of the adapter 102.

Figure 2B:
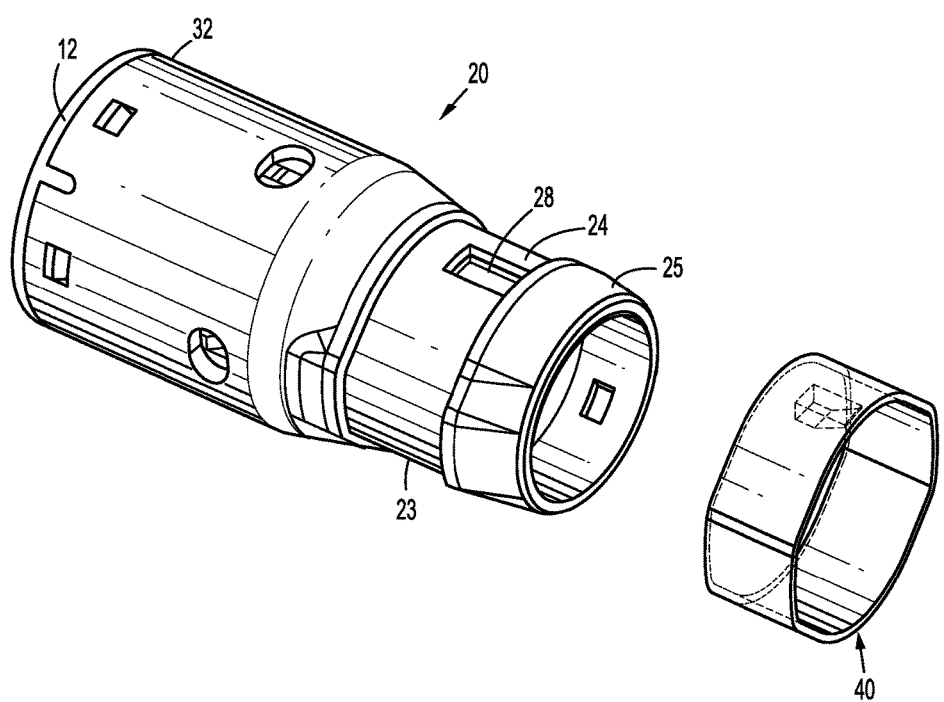
FIG. 2B is a perspective view of the loading unit of FIG. 1A with the locking collar separated therefrom.

Referring also to FIG. 2B, the shell assembly 20 includes a proximal end portion 22 that defines a cylindrical opening 21 (FIG. 2A) for receiving the distal end portion 110 of the adapter 102 and a distal end 32 that defines a receptacle 34 for receiving and supporting the staple cartridge 12 (FIG. 4). The proximal end portion 22 of the shell assembly 20 includes a recessed annular ring 23 (FIG. 2B) that defines a groove 24 sized to receive the locking collar 40. In embodiments, the locking collar 40 has a thickness equal to the depth of the groove 24 such that the locking collar 40 forms a continuous or smooth surface with the outer surface of the proximal end portion 22 of the shell assembly 20. The annular ring 23 defines a lock opening 28 (FIG. 5) that receives a portion of the locking collar 40 as detailed below and defines inner and outer surfaces 23a, 23b.

The proximal end portion 22 of the shell assembly 20 supports a collar retainer 25 that retains the locking collar 40 within the groove 24. The collar retainer 25 may also be tapered to provide a smooth transition from the outer diameter of the locking collar 40 to the distal end portion 110 of the adapter 102 (or alternatively, the instrument 700 FIG. 1B). The collar retainer 25 may include locking features 26 (FIG. 2A) which secure the collar retainer 25 to the proximal end portion 22 of the shell assembly 20. It is contemplated that the collar retainer 25 may be secured to the proximal end portion 22 of the shell assembly 20 by any known means including, but not limited to, press-fitting or ultrasonic welding tabs and interlocking structure. It is also contemplated that the collar retainer 25 may be integrally formed with the proximal end portion 22 of the shell assembly 20.

With reference to FIGS. 3-6, the locking collar 40 includes a generally annular body 42 that is sized to fit within the groove 24 of the proximal end portion 22 of the shell assembly 20 and a lock 44 that extends radially inward from the annular body 42. The locking collar 40 is positioned about the proximal end portion 22 such that the lock 44 is radially aligned with the lock opening 28. The lock 44 includes a proximal step 45, a distal step 48, and an angled surface 46 positioned between the proximal and distal steps 45, 48. The proximal step 45 extends radially inward a first distance from the longitudinal axis A-A of the shell assembly 20 and the distal step 48 extends radially inward a second distance from the longitudinal axis A-A of the shell assembly 20 less than the first distance. The lock 44 may also include a landing 47 between the angled surface 46 and the distal step 48 that is substantially parallel to the longitudinal axis A-A of the shell assembly 20. The distal step 48 is positioned to engage a distal wall defining the lock opening 28 of the annular ring 23 of the shell assembly 20. The proximal step 45 is positioned adjacent a proximal wall of the lock opening 28 to longitudinally fix the locking collar 40 to the proximal end portion 22 of the shell assembly 20.

The locking collar 40 may be made of a resilient material. For example, the locking collar 12 may be formed of a resilient plastic material using an injection molding process. However, it is contemplated the locking collar 40 may be formed of other suitable materials including, but not limited to, spring steel, stainless steel, or wire.

With particular reference to FIG. 6, the locking collar 40 includes first and second release surfaces 41a, 41b. Lock 44 may be positioned on the annular body 42 halfway between the first and second release surfaces 41a, 41b. In a locked configuration, the annular body 42 defines a generally elliptical shape where the annular body 42 has a width along a first axis B-B (from the first release surface 41a to the second release surface 41b) that is greater than its height along a second axis C-C (from the lock 44 to the side opposing the lock 44). The annular body 42 is biased towards the locked configuration such that the lock 44 when positioned about the annular ring 23 penetrates the inner surface 23a of the annular ring 23 (FIG. 5) and extends into the window 112 of the distal end portion 110 of the adapter 102 to secure the loading unit 10 to the surgical instrument, e.g., the adapter 102. The annular body 42 is positioned within the groove 24 about the annular ring 23 such that the distal step 48 (FIG. 5) engages a distal wall 112a (FIG. 5) defining the window 112 of the adapter 102 to longitudinally fix the shell assembly 20 to the distal end portion 110 of the adapter 102 of the surgical instrument. It will be appreciated that the lock opening 28 of the annular ring 23 of the shell assembly 20 is aligned with the window 112 of the adapter 102 in the locked configuration to permit the lock 44 to pass through the lock opening 28 and the window 112 as detailed above.

FIGS. 7 and 8 illustrate the locking collar 40 in an unlocked configuration with the annular body 42 defining a generally elliptical shape where the height is greater than the width. The release surfaces 41a, 41b can be manually pressed together to move the locking collar 40 to the unlocked configuration. In the unlocked configuration, the lock 44 is moved radially outward by distance "D" shown in FIG. 7 such that the lock 44 is positioned radially outward from the inner surface 23a of the annular ring 23 (FIG. 5). The distance "D" is greater than the distance that the lock 44 extends into the window 112 of the adapter 102 such that in the unlocked configuration, the loading unit 10 is disengaged and removable from the distal end portion 110 of the adapter 102 when the locking collar 40 is in an unlocked configuration. It is contemplated that the distance "D" may be greater than the second distance that the distal step 48 of the lock 44 extends radially inward such that in the unlocked configuration, the lock 44 is removed from the window 112 of the adapter 102 and the lock opening 28 of the proximal end portion 22 of the shell assembly 20. As shown, in the unlocked configuration, the height is greater than the width; however, it is contemplated that in the unlocked configuration the width may be greater than the height with the lock 44 moved outward by the distance "D".

Referring back to FIGS. 2-4, to couple the loading unit 10 to the surgical instrument, e.g., the adapter 102, the loading unit 10 is aligned with the adapter 102 such that the distal end portion 110 of the adapter 102 is positioned within the cylindrical opening 21 of the proximal end portion 22 with the window 112 of the adapter 102 radially aligned with the lock opening 28 of the annular ring 23 and the lock 44 of the locking collar 40. The outer surface of the locking collar 44 may include visual or tactile indicia as to the location of the lock 44. With the loading unit 10 aligned with the adapter 102, the loading unit 10 is moved proximally over the distal end portion 110 of the adapter 102 until the lock 44 is received within the window 112 of the adapter 102. It will be appreciated that the lock 44 passes through the lock opening 28 to be received within the window 112 of the adapter 102. As the loading unit 10 is moved proximally over the distal end 110 of the adapter 102, the angled surface 46 of the lock 44 engages the distal end portion 110 of the adapter 102 to transition, i.e., perform a camming action to deform, the locking collar 40, against the natural resilience of the annular body 42, from the locked configuration towards an unlocked configuration until the window 112 moves into alignment with the lock 44. When the window 112 moves into alignment with the lock 44, the lock 44 is snaps into the window 112. The snapping movement of the locking collar 40 may provide visual or audible indicia that the lock 44 is received within the window 112. It will be appreciated that the natural resilience of the annular body 42 of the locking collar 40 urges the lock 44 through the window 112 in the adapter 102. When the lock 44 is positioned within the window 112, the distal step 48 of the locking collar 40 engages the wall 112a of the adapter 102 defining the window 112 to longitudinally secure the shell assembly 20 of the loading unit 10 to the adapter 102. In addition, when the lock 44 is received within the window 112, the lock 44 prevents the loading unit 10 from rotating or twisting (i.e., radially secure) relative to the surgical instrument, e.g., the adapter 102.

With the loading unit 10 is coupled to the surgical instrument, e.g., the adapter 102, the surgical instrument and loading unit 10 may be used to perform a surgical procedure. After surgical procedure is completed, the loading unit 10 can be decoupled or detached from the surgical instrument as will be discussed in detail below. When the loading unit 10 is decoupled from the surgical instrument, another loading unit may be coupled to the surgical instrument for continued use in the surgical procedure, the surgical instrument may be sterilized for use in another surgical procedure, or the surgical instrument may be discarded. In addition, the loading unit 10 may be sterilized for use in another surgical procedure or may be discarded.

To decouple or remove the loading unit 10 from the surgical instrument, e.g., the adapter 102, the locking collar 40 is transitioned to the unlocked configuration by compressing the first and second release surfaces 41a, 41b towards one another along the first axis B-B, as represented by arrows "F" shown in FIG. 7. It is contemplated, that the locking collar 40 may be transitioned to the unlocked configuration by compressing only one of the first and second release surfaces 41a, 41b towards the other release surface 41a, 41b as shown in FIG. 7. With the locking collar 40 in the unlocked configuration, the shell assembly 20 can be removed from engagement with the distal end portion 110 of the adapter 102 by moving the shell assembly 20 axially in relation to the adapter 102.

Referring now to FIGS. 9-12, another locking collar 140 is provided in accordance with the present disclosure and includes a lock 44 and an annular body 142. The lock 44 of locking collar 140 is substantially similar to the lock 44 of the locking collar 40 as detailed above and will not be discussed further below except for how it relates to locking collar 140. The annular body 142 of the locking collar 140 is similar to the annular body 42 of the locking collar 40 detailed above, as such only the differences will be detailed below for reasons of brevity.

The annular body 142 is split at one side to form first and second release surfaces or end portions 144, 146 which are moveably positioned in relation to each other such that the diameter of the locking collar 140 can be selectively changed, as described below. The first end portion 144 extends in a first direction about the circumference of the annular body 142 and the second end portion 146 extends in a second direction opposite the first direction about the circumference of the annular body 142. The first and second release surfaces 144, 146 are positioned about the annular body 142 opposing the lock 44. Each of the first and second end portions 144, 146 has an end 145, 147 that defines an engagement window 149 adjacent the annular body 142. Each of the first and second end portions 144, 146 has a thickness along the longitudinal axis of the loading unit 10 (FIG. 1) approximately half the thickness of the annular body 142 such that the first and second end portions 144, 146 overlap one another about the circumference of the annular body 142.

With particular reference to FIGS. 10 and 12, the locking collar 140 is formed of a resilient material having a natural resiliency to urge the locking collar 140 towards a locked configuration (FIG. 10). In the locked configuration, the annular body 142 defines a substantially circular cross-section in a plane transverse to the longitudinal axis of the loading unit 10 (FIG. 1). In an unlocked configuration of the locking collar 140 (FIG. 12), the annular body 142 defines a generally elliptical cross-section in a plane transverse to the longitudinal axis of the loading unit 10. In the unlocked configuration, the lock 44 is moved a distance "E'" away from the first and second end portions 144, 146. The locking collar 140 is transitioned towards the unlocked configuration by urging the ends 145, 147 of the first and second end portions 144, 146, respectively, towards one another as represented by the arrows "F." As the ends 145, 147 are urged towards one another, the annular body 142 moves the lock 44 the distance "E" away from the ends 145, 147. The first and second end portions 144, 146 may include visual or tactile indicia in the form of arrows (FIG. 9) as to the direction to urge the first and second end portions 144, 146 to move the locking collar 140 towards the unlocked configuration.

With reference to FIGS. 13-19, another loading unit 210 is provided in accordance with the present disclosure. As detailed below, the loading unit 210 includes retention tabs 252, 254 that are received within retention slots 238, 264 of a shell assembly 220 to prevent one side of a locking collar 240 from moving outward of the shell assembly 220 when release surfaces 241a, 241b of the locking collar 240 are compressed or squeezed. By limiting outward movement of one side of the locking collar 240, outward movement of the opposite side of the locking collar 240 is amplified to reduce the extent of inward movement of the release surfaces 241a, 241b necessary to release the loading unit 210 from a distal end of an instrument as discussed in detail below. The loading unit 210 includes the shell assembly 220, the locking collar 240, and the retention ring 260. The shell assembly 220 is similar to the shell assembly 20 detailed above. As such, discussion of similar features will be limited for reasons of brevity.

Figure 13:
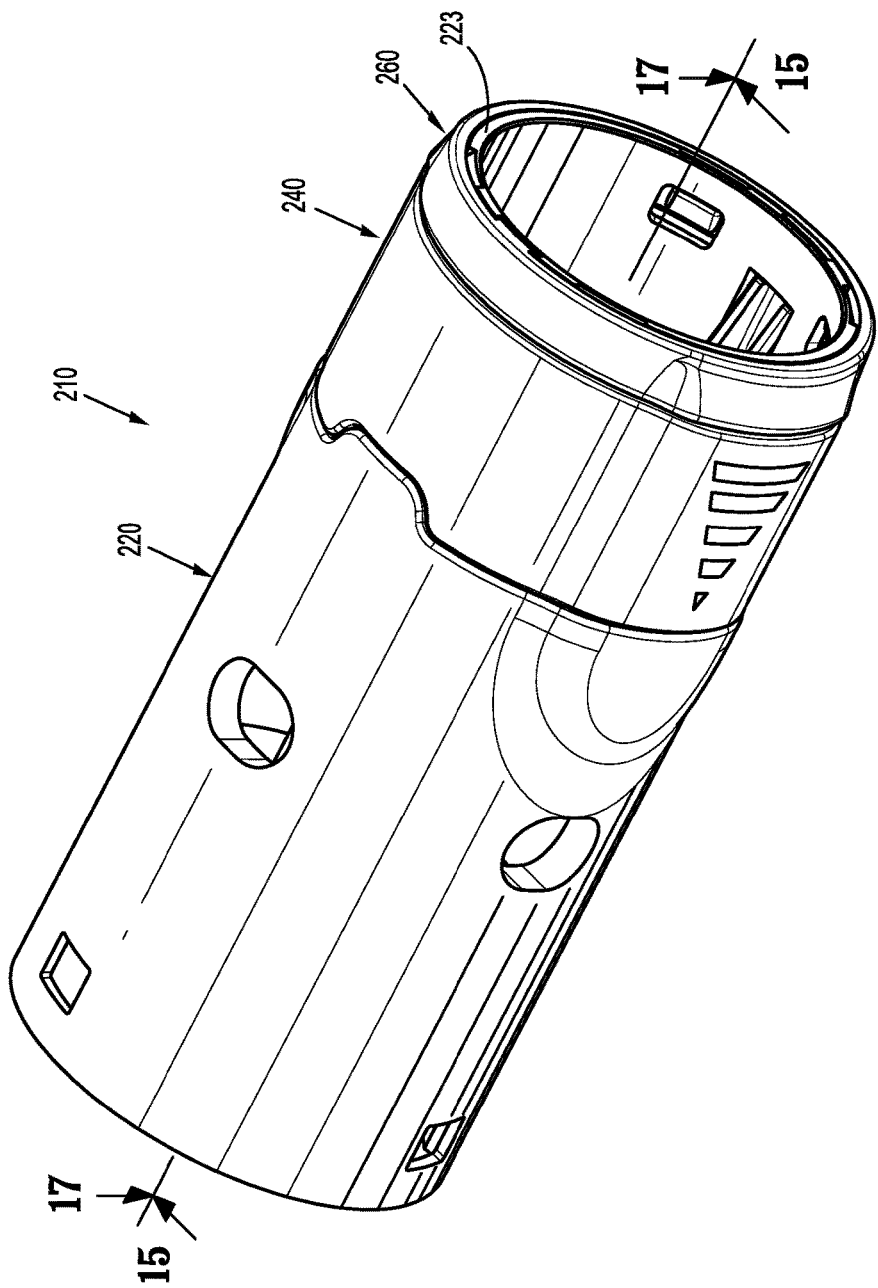
FIG. 13 is a perspective view of another loading unit provided in accordance with the present disclosure.
Figure 14A:
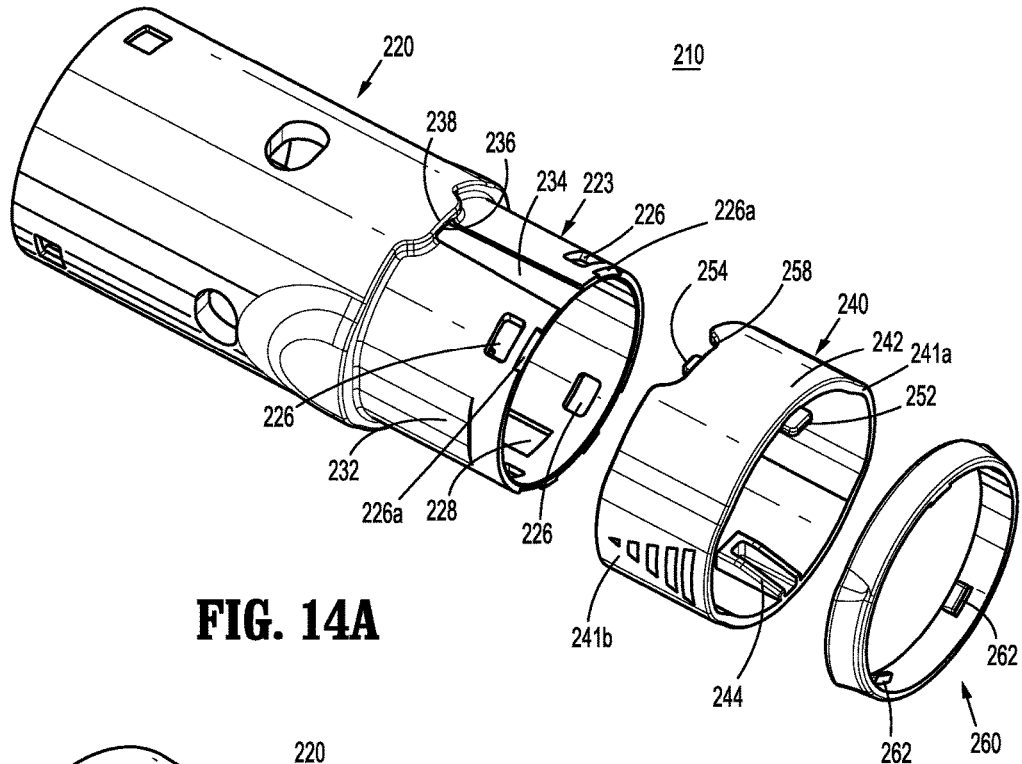
FIGS. 14A and 14B are exploded perspective views of the loading unit of FIG. 13.
Figure 14B:
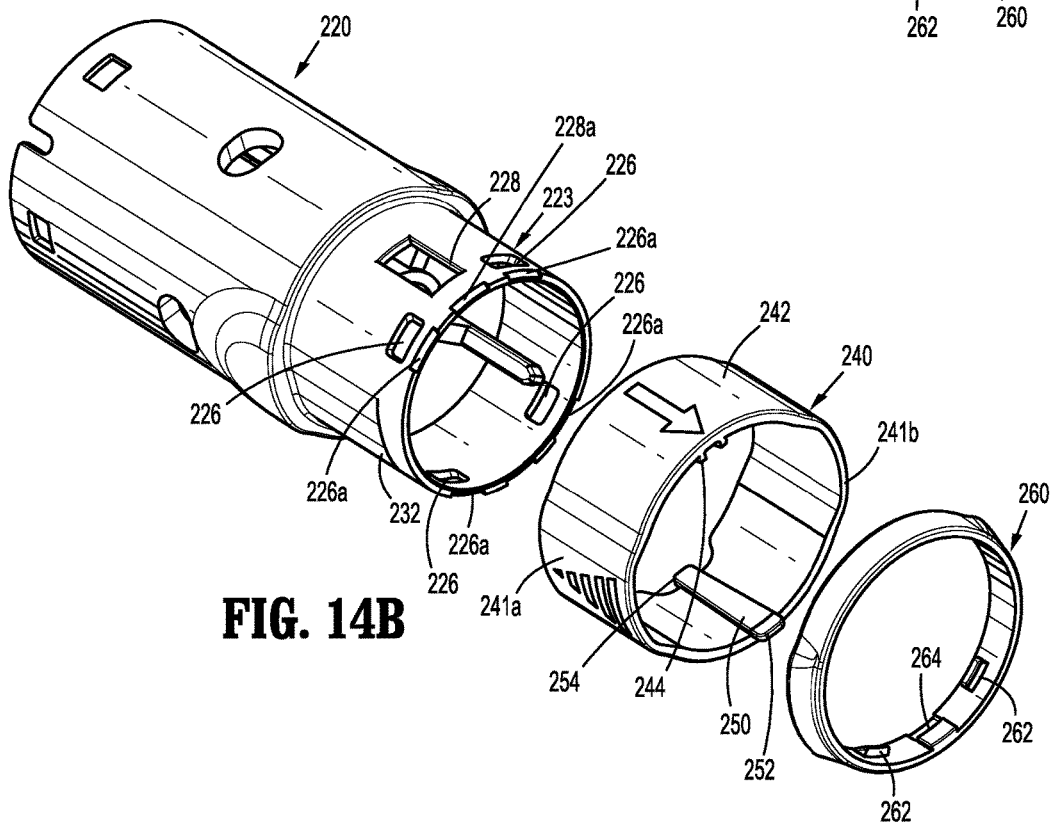

Referring now to FIGS. 13-14B, the shell assembly 220 includes a proximally extending annular ring 223. The annular ring 223 defines retention openings 226, a lock opening 228, relief grooves 232, and a retention groove 234. The retention openings 226 are spaced about the annular ring 223. It is contemplated that the retention openings 226 may be equally or unequally spaced about the annular ring 223. The relief grooves 232 are defined about the annular ring 223 such that the relief grooves 232 diametrically oppose one another. The lock opening 228 may be positioned halfway between the relief grooves 228. The relief grooves 232 may be flats such that the curvature of the annular ring 223 flattens to form the relief grooves 232. The retention groove 234 is positioned between relief grooves 232 opposite the lock opening 228. The retention groove 234 extends in a direction parallel to the longitudinal axis of the shell assembly 220 and may be positioned halfway between the relief grooves 232. The shell assembly 220 includes a proximally extending retention cover 238 that extends partially over the retention groove 234 to define a retention slot 236.

The locking collar 240 includes release surfaces 241a, 241b, a generally annular body 242, a lock 244, and a retention rib 250 (FIG. 14B). The release surfaces 241a, 241b, the body 242, and the lock 244 are similar to the release surfaces 41a, 41b, body 42, and the lock 44, respectively, detailed above with regard to locking collar 40 and will not be described herein below for reasons of brevity. The annular body 242 is sized to slidably receive the annular ring 223 of the shell assembly 220. The retention rib 250 extends inwardly from an inner surface of the body 242 between the release surfaces 241a, 241b and opposing the lock 244. The retention rib 250 includes proximal and distal retention tabs 252, 254 extending from the body 242. In embodiments, the distal side of the body 242 defines a retention cutout 258 (FIG. 14A) that is sized to receive the retention cover 238 of the shell assembly 220. As described in greater detail below, the retention rib 250 is received within the retention groove 234 to rotationally align or index the locking collar 240 with the shell assembly 220.

The retention ring 260 is positioned over the annular ring 223 of the shell assembly 220 at a position proximal to the locking collar 240 to retain the locking collar 240 over the annular ring 223 of the shell assembly 220. The retaining ring 260 includes locking tabs 262 and defines a retaining slot 264 (FIG. 14B). The locking tabs 262 extend from the inner surface of the retention ring 260 and are sized to be received within respective retention openings 226 of the annular ring 223. Each of the locking tabs 262 defines a distally facing wedge that is configured to flex the retention ring 260 outward as the retention ring 260 is slid over the annular ring 223 until the locking tabs 262 are aligned with the retention openings 226. When the locking tabs 262 are aligned with the retention openings 226, the locking tabs 262 snap through the retention openings 226 to fix the retention ring 260 to the annular ring 223. The locking tabs 262 of the retention ring 260 and the retention openings 226 of the annular ring 223 are positioned about the annular ring 223 such that when the locking tabs 262 are received within the retention openings 226, the retention slot 264 is rotationally aligned with the retention groove 234 of the annular ring 223. The annular ring 223 may define chamfers 226a at a distal end of the annular ring 223 to assist in rotationally aligning the retention ring 260 with the annular ring 223 and to assist in sliding the retention ring 260 over the annular ring 223.

Figure 15:
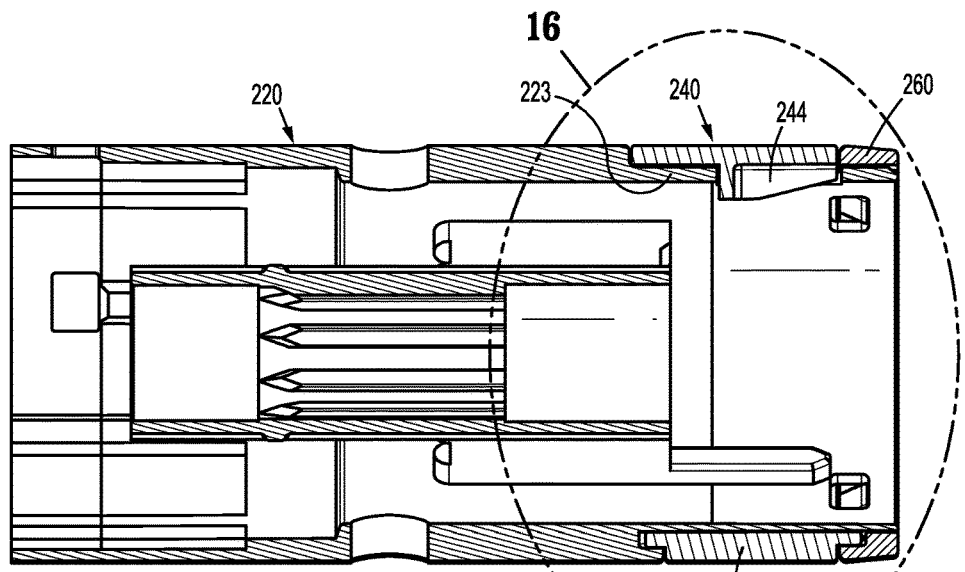
FIG. 15 is a cross-sectional view taken along the section line 15-15 of FIG. 13.
Figure 16:
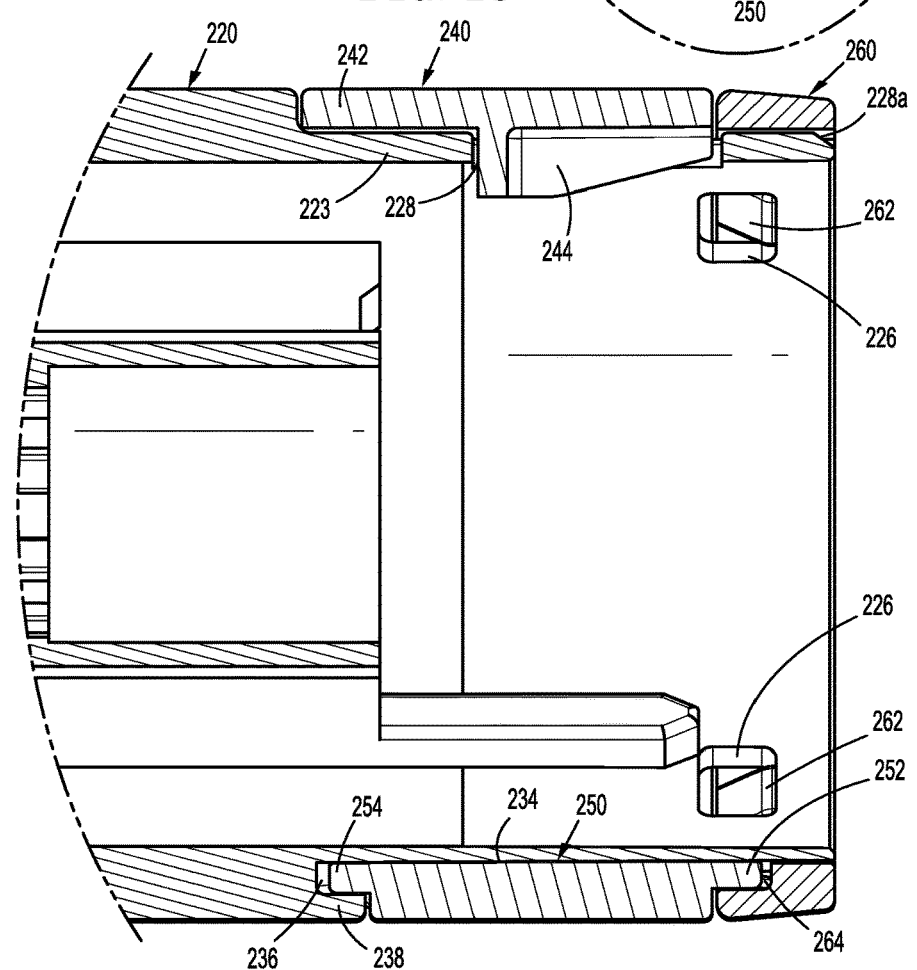
FIG. 16 is an enlarged view of the indicated area of detail of FIG. 15.
Figure 17:
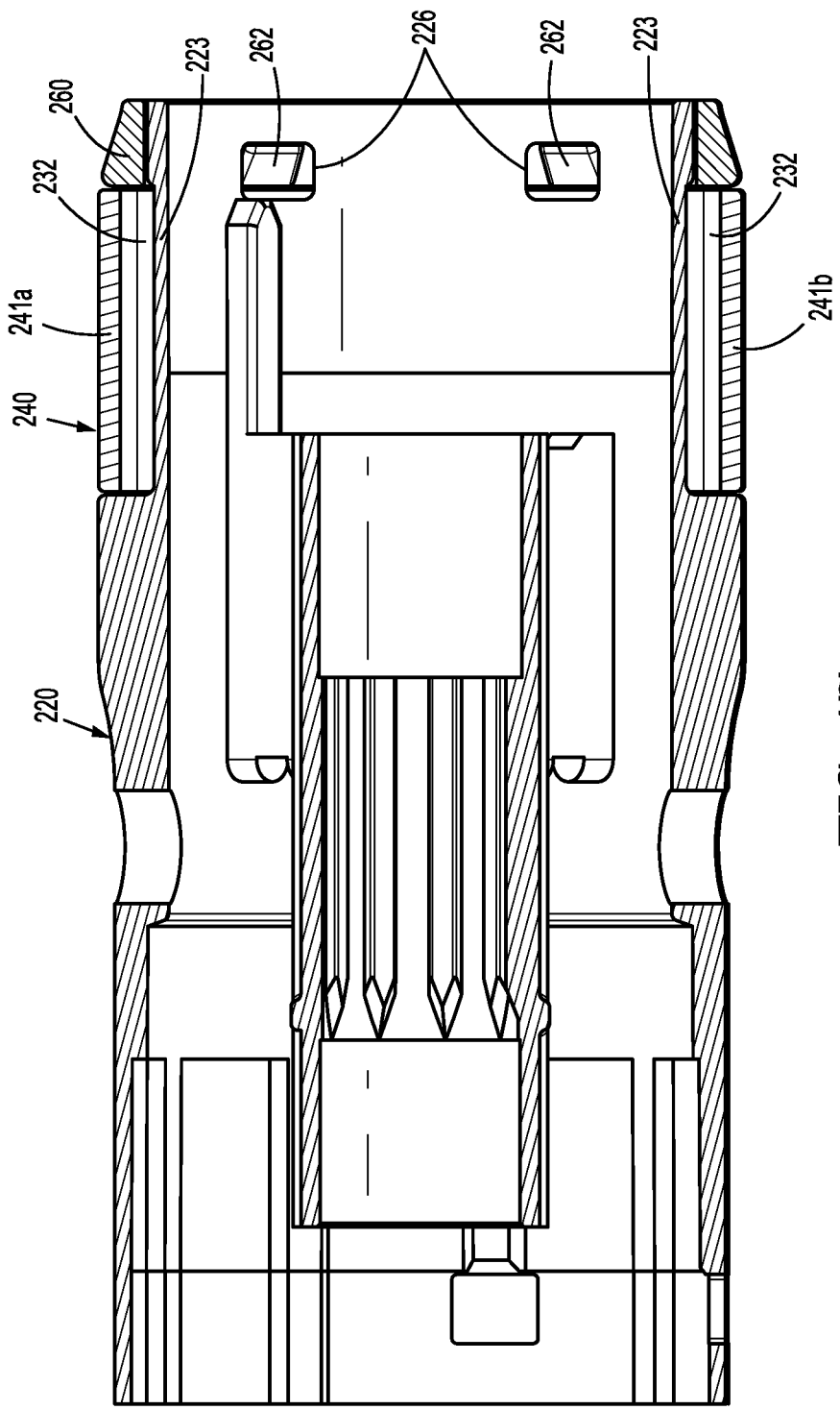
FIG. 17 is a cross-sectional view taken along the section line 17-17 of FIG. 13.

Referring also to FIGS. 15-17, a method of assembling the loading unit 210 is disclosed in accordance with the present disclosure. Initially referring to FIGS. 14A and 14B, the locking collar 240 is aligned with the shell assembly 220 such that the retention rib 250 of the locking collar 240 is aligned with the retention groove 234 defined in the annular ring 223 of the shell assembly 220. When the locking collar 240 is aligned with the shell assembly 220, the locking collar 240 is slid distally over the annular ring 223 with the retention rib 250 sliding within the retention groove 234. The locking collar 240 is slid distally over the annular ring 223 until the lock 244 of the locking collar 240 is disposed within the lock opening 228 of the annular ring 223. The annular ring 223 may define a lock chamfer 228a (FIG. 16) axially aligned with the lock opening 228 to assist in rotationally aligning the locking collar 240 with the annular ring 223 and to assist in sliding the locking collar 240 over the annular ring 223. As the locking collar 240 is slid distally over the annular ring 223, the lock 244 will abut the annular ring 223. To facilitate placement of the locking collar 240 on the annular ring 223, the release surfaces 241a, 241b can be pressed towards one another as the locking collar 240 is slid over the annular ring 223 to flex the body 242 of the locking collar 240 to move the lock 244 outward beyond the annular ring 223. When the lock 244 is aligned with the lock opening 228, the release surfaces 241a, 241b are released such that the lock 244 snaps through the lock opening 288 as shown in FIG. 16.

With particular reference to FIG. 16, as the locking collar 240 is slid over the annular ring 223, the retention rib 250 is received within the retention groove 234 of the annular ring 223 until the distal retention tab 254 is received within the retention slot 236 of the shell assembly 220. With the locking collar 240 positioned about the annular ring 223, the retention ring 260 is slid distally over the annular ring 223 to secure the locking collar 240 on the annular ring 223. In order to slide the retention ring 260 about the annular ring 223, the retention ring 260 is radially aligned with the annular ring 223 and the locking collar 240 such that the retention slot 264 of the retention ring 260 is aligned with the proximal retention tab 252 of the retention rib 250 and the retention groove 234 of the shell assembly 220. When the retention ring 260 is positioned over the annular ring 223, the locking tabs 262 snap through the retention openings 226 of the annular ring 223 to fix the retention ring 260 to a proximal end of the annular ring 223.

Figure 18:
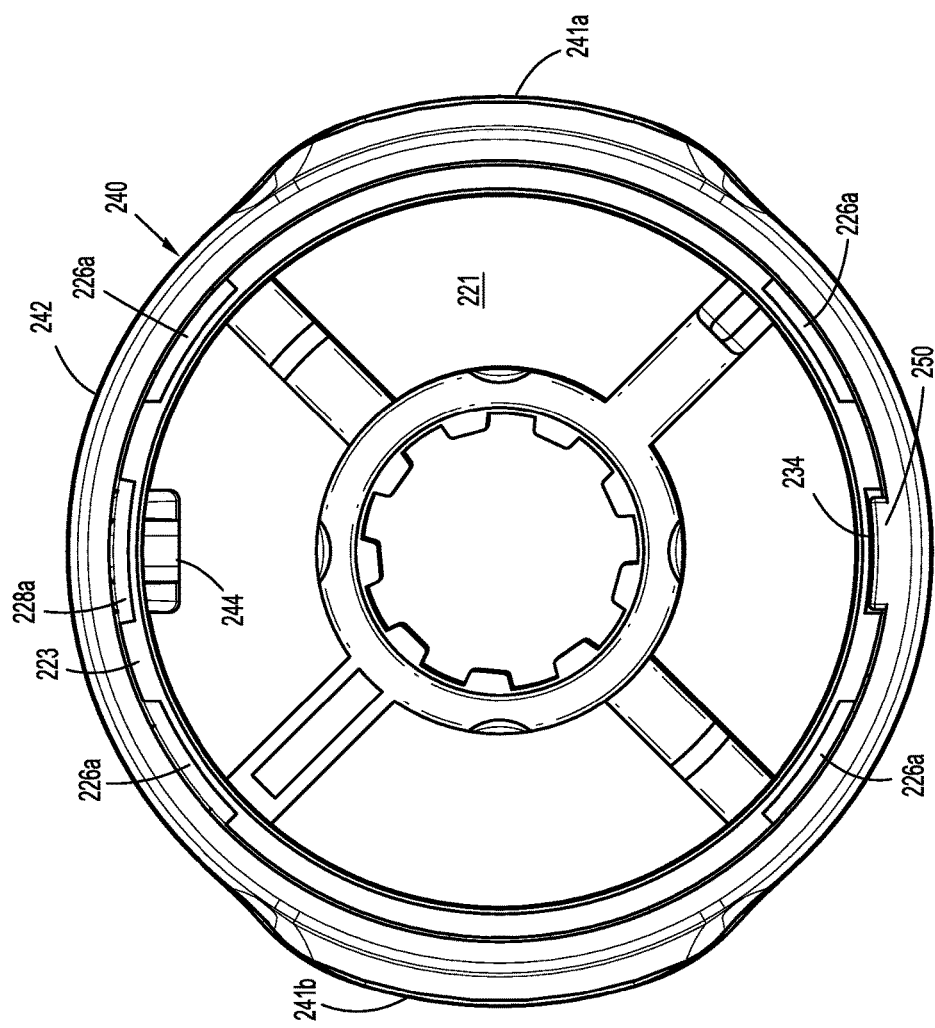
FIG. 18 is a rear view of the loading unit of FIG. 13 with the locking collar in a locked configuration.
Figure 19:
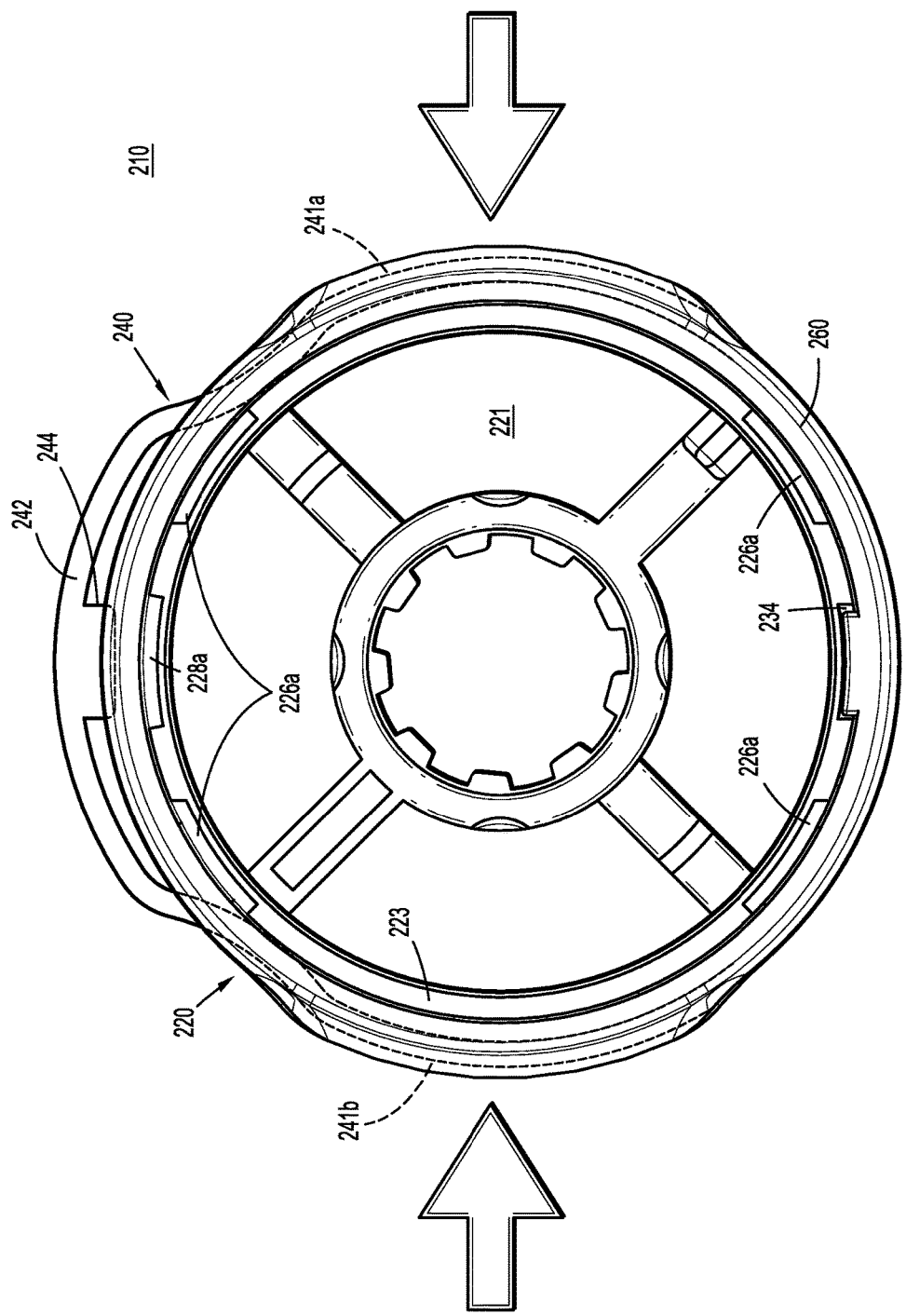
FIG. 19 is a rear view of the loading unit of FIG. 13 with the locking collar in an unlocked configuration.

Referring to FIGS. 17-19, the relief grooves 232 of the annular ring 223 provide clearance under the release surfaces 241a, 241b of the body 242 of the locking collar 240 to facilitate inward movement of the release surfaces 241a, 241b as detailed below. When the release surfaces 241a, 241b are pressed inwardly as shown in FIG. 19, the retention tabs 252, 254 (FIG. 16) of the locking collar 240 prevent the side of the body 242 of the locking collar 240 opposite the lock 244 from moving outwardly. As such, when the release surfaces 241a, 241b are pressed inwardly, only the side of the locking collar 240 supporting the lock 244 moves outwardly. By retaining or preventing the side of the body 242 opposite the lock 244 from moving outwardly, the extent of inward movement of the releases surfaces 241a, 241b required to displace or move the lock 244 out of the lock opening 228 is reduced when compared to locking collar 40, detailed above.

As shown in FIG. 19, when both release surfaces 241a, 241b are moved inwardly, the lock 244 is moved outwardly such that the lock 244 is positioned outside of a cylindrical opening 221 defined by the annular ring 223 and beyond an outer surface of the annular ring 223. This allows the loading unit 210 to be detachable or slidable off a distal end of an adapter or surgical instrument as detailed above. It is contemplated that the relief grooves 232 can be configured such that it is necessary to move only one of the release surfaces 241a, 241b inwardly to move the lock 244 outwardly to allow detachment of the loading unit 210 from a distal end of an adapter or surgical instrument as detailed above.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. The present disclosure is not limited to circular stapling loading units, but has application to loading units for linear stapling or other types of instruments, such as electrocautery or ultrasonic instruments. Therefore, the above description should not be construed as limiting, but merely as exemplifications of particular embodiments. Those skilled in the art will envision other modifications within the scope of the claims appended hereto.

What is claimed:

1. A loading unit and locking collar assembly, the assembly comprising:
   a shell assembly having a proximally extending annular ring that defines a cylindrical opening, the annular ring defining a lock opening therethrough, the shell assembly defining a first retention slot adjacent the annular ring on an opposite side of the annular ring from the lock opening;
   a locking collar positioned about the annular ring, the locking collar having a body, a lock, and a first retention tab, the body including at least one release surface, the lock extending from an inner surface of the body spaced from the at least one release surface, the locking collar having a locked configuration wherein the lock extends through the lock opening into the cylindrical opening and an unlocked configuration wherein the lock is disposed outwardly of the cylindrical opening, the first retention tab being received within the first retention slot to prevent a side of the locking collar opposite the lock from moving outwardly in relation to the annular ring when the at least one release surface is pressed inwardly towards the annular ring.

2. The assembly according to claim 1, wherein the at least one release surface includes two releases surfaces, the two release surfaces being positioned on opposite sides of the body and being moveable inwardly towards one another to transition the locking collar to the unlocked configuration.

3. The assembly according to claim 2, wherein the annular ring defines a relief groove adjacent each of the two release surfaces, the relief grooves allowing inward movement of the body of the locking collar in the area of the release surfaces.

4. The assembly according to claim 1, wherein the body is resilient and the resilience of the body urges the locking collar towards the locked configuration.

5. The assembly according to claim 1, further comprising a retention ring positioned about the annular ring proximal of the locking collar, the retention ring defining a second retention slot.

6. The assembly according to claim 5, wherein the locking collar includes a second retention tab received within the second retention slot to prevent the side of the locking collar opposite the lock from moving outwardly when the at least one release surface is pressed inwardly towards the annular ring.

7. The assembly according to claim 6, wherein the first and second retention tabs are axially aligned with one another.

8. The assembly according to claim 6, wherein the annular ring defines a retention groove that extends in a direction parallel to a longitudinal axis of the shell assembly, and wherein the first and second retention tabs extend from opposite ends of a retention rib that extends inwardly from an inner surface of the body, the retention rib being disposed in the retention groove.

9. The assembly according to claim 8, wherein the shell assembly includes a cover extending distally over the retention groove to define the first retention slot.

10. The assembly according to claim 9, wherein the body of the locking collar defines a cutout positioned adjacent the first retention tab, the cutout being sized to receive the cover of the shell assembly.

11. The assembly according to claim 5, wherein the annular ring defines retention openings, and wherein the retention ring includes locking tabs extending from an inner surface thereof, each of the locking tabs being received in a respective one of the retention openings to fix the retention ring to the annular ring.

12. The assembly according to claim 11, wherein the retention openings are unequally spaced about the annular ring.

13. The assembly according to claim 11, wherein the locking tabs define a wedge shape with an angled surface of the wedge facing distally.

14. The assembly according to claim 11, wherein a proximal end of the annular ring defines chamfers, each of the chamfers being axially aligned with one of the retention openings.

15. The assembly according to claim 1, wherein a proximal end of the annular ring defines a chamfer axially aligned with the lock opening.

16. A surgical system comprising:
a surgical instrument including a distal end defining a lock window;
a shell assembly having a proximally extending annular ring that defines a cylindrical opening, the annular ring defining a lock opening therethrough, the shell assembly defining a first retention slot adjacent the annular ring on an opposite side of the annular ring from the lock opening, the distal end of the surgical instrument received within the cylindrical opening with the lock opening radially aligned with the lock window; and
a locking collar positioned about the annular ring, the locking collar having a body, a lock, and a first retention tab, the body including the at least one release surface, the lock extending from an inner surface of the body spaced from the at least one release surface, the locking collar having a locked configuration wherein the lock extends through into the lock window to secure the shell assembly to the distal end of the surgical instrument and an unlocked configuration wherein the lock is disengaged from the lock window such that the shell assembly is detachable from the distal end of the surgical instrument, the first retention tab being received within the first retention slot to prevent a side of the locking collar opposite the lock from moving outwardly in relation to the annular ring when the at least one release surface is pressed inwardly towards the annular ring.

17. A method of using a loading unit, the method comprising:
aligning a locking collar with a shell assembly; and
sliding the loading unit distally over a proximally extending annular ring of the shell assembly, a lock of the locking collar engaging the annular ring such that the lock is moved outwardly towards an unlocked configuration of the locking collar until the lock is aligned with a lock opening defined through the annular ring, resilience of a body of the locking collar urging the locking collar towards a locked configuration of the locking collar to move the lock through the lock opening, a retention tab of the locking collar positioned on an opposite side of the locking collar from the lock sliding into a retention slot defined by the shell assembly to prevent the opposite side of the locking collar from moving outwardly.

18. The method according to claim 17, further comprising attaching the loading unit to a distal end of a surgical instrument including:
aligning the loading unit with the distal end of the surgical instrument; and
sliding the loading unit over the distal end of the surgical instrument such that the lock of the locking collar engages the distal end of the surgical instrument, the distal end moving the lock outwardly to urge the locking collar towards the unlocked configuration until the lock is aligned with a locking window defined in the distal end of the surgical instrument, the lock being urged through the locking window by resilience of the body of the locking collar to secure the loading unit to the distal end of the surgical instrument.

19. The method according to claim 18, further comprising actuating a shell assembly of the loading unit with the surgical instrument after the loading unit is attached to the distal end of the surgical instrument.

20. The method according to claim 19, further comprising detaching the loading unit from the distal end of the surgical instrument after actuating the shell assembly including:
moving a release surface of the locking collar inwardly to move the lock outwardly such that the lock is disengaged from the locking window of the distal end of the surgical instrument, the retention tab of the locking collar engaging the shell assembly to prevent the side of the locking collar opposite the lock from moving outwardly in response to moving the release surface of the locking collar inwardly; and sliding the loading unit off of the distal end of the surgical instrument.

\* \* \* \* \*